(12) United States Patent
Kasahara (10) Patent No.: US 6,318,373 B1
(45) Date of Patent: Nov. 20, 2001

(54) CORRECTIVE SUPPORTER FOR CORRECTING HALLUX VALGUS AND DIGITUS VERUS MINIMI DEFORMITY

(76) Inventor: Iwao Kasahara, 3734-6, Totsukacho, Totsuka-ku, Yokohama-shi, Kanagawa-ken (JP)

( * ) Notice: Subject to any disclaimer, the term of this patent is extended or adjusted under 35 U.S.C. 154(b) by 0 days.

(21) Appl. No.: 09/665,209

(22) Filed: Sep. 18, 2000

(30) Foreign Application Priority Data

Sep. 20, 1999 (JP) .................................................. 11-304488
Sep. 28, 1999 (JP) .................................................. 11-312819

(51) Int. Cl.⁷ ...................................................... A61F 13/06
(52) U.S. Cl. ............................................. 128/894; 602/30
(58) Field of Search ................................... 128/846, 869, 128/882, 892, 893; 602/30

(56) References Cited

U.S. PATENT DOCUMENTS

| 3,556,091 | * | 1/1971 | Haig | 602/30 |
| 4,207,880 | * | 6/1980 | Zinkovich | 602/30 |
| 5,437,616 | * | 8/1995 | Kasahara | 602/30 |
| 5,802,737 | * | 9/1998 | Beppu | 36/115 |

FOREIGN PATENT DOCUMENTS

| 2-12094 | 3/1990 | (JP) . |
| 7-13699 | 4/1995 | (JP) . |
| 7-27926 | 6/1995 | (JP) . |
| 2534781 | 2/1997 | (JP) . |

* cited by examiner

*Primary Examiner*—Michael A. Brown
(74) *Attorney, Agent, or Firm*—Jordan and Hamburg LLP (57) ABSTRACT

A corrective supporter provides for correction of Hallux Valgus and Digitus Varus Minimi to allow the stable maintenance of outer and inner vertical and lateral arches of a plantar sole. The corrective supporter includes a pushing band to push against the inward or outward prominent metatarsophalangeal to the normal positions, and two resilient reinforcements, the first resilient reinforcement which is located between the first toe and the second or into which the first toe is fitted such that the first toe moves away from the second by the outward push force or pull force, and the second resilient reinforcement which is located between the fifth toe and the fourth or into which the fifth toe is fitted such that the fifth toe moves away from the fourth toe by the outward push force, or the pull force. The maintenance of the outer and inner vertical and lateral arches permit the wearer to walk well, and eliminates a problem of slippage and rotation of the corrective supporter on the foot surface during walking.

8 Claims, 6 Drawing Sheets

CORRECTIVE SUPPORTER FOR CORRECTING HALLUX VALGUS AND DIGITUS VERUS MINIMI DEFORMITY

FIELD OF THE INVENTION

The present invention relates to a corrective supporter for correcting hallux valgus and digitus varus minimi deformities, and particularly to a corrective supporter having a pushing band to push against prominent first and fifth metatasopharangeal joints that protrude from the correct position on the foot, and resilient reinforcements for separating a first toe which might approach the second, from the latter, and the fifth which might approach the fourth, from the latter so as to reinforce the push force of the pushing band.

BACKGROUND OF THE INVENTION

The present invention is intended to eliminate problems with Hallux Vulgus and Toe Varus, which are shock waves and buckling waves that were found as a result of my study on human feet.

It is generally known that when people step paces, the weight is taken on three points of the heel, the first toe, and the fifth toe. It will be understood that the foot is subjected to the shock in response to the weight which is moved upward and downward during the contact with and the separation from the earth, but it must be known still that at the time buckling waves are also generated. The shock and buckling waves, which are generated by the severe vibrations of the foot are similar to waves of vertical and lateral shakes that are generated by earthquakes, and become harmful stresses traveling to the body over and over for Hallux Valgus and Digitus Varus Minimi.

The foot sole, which is protected from the shock buckling waves is formed with the plantar arch having three arches of the inner and outer vertical arches with respect to the median human body line, and the lateral arch. Upon steps of the walking people, the actions of absorbing the shock waves are comprised of separations of the first toe from the second toe, which are performed by the inner and outer vertical arches that prevent inward and outward displacements of the foot, respectively, while the actions of absorbing the buckling waves are performed by tightening a lateral metatatasal ligament, lateral arch which might be tensioned and constitutes the metatarsophalangeal joints. Thus, movements in the human weight are maintained by the actions from the lateral and vertical arches that make the harmful shock and buckling harmless and balance.

Figure 9:
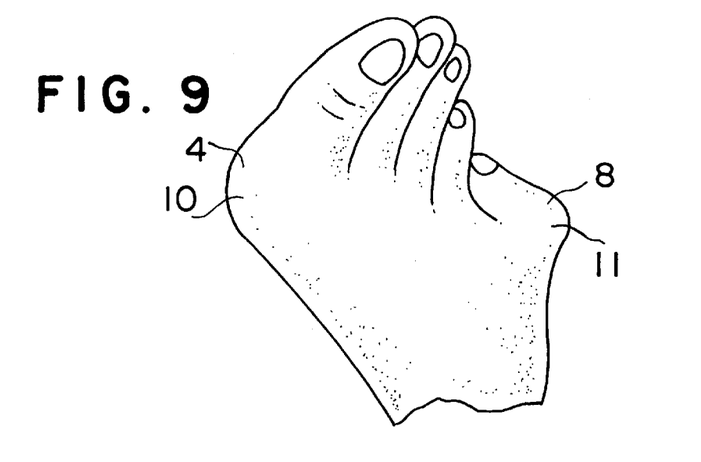
FIG. 9 is an external oblique view of a foot with Hallux Valugus and Digitus Varus Minimi.

Referring to FIG. 9, a deformed right foot with Hallux Valgus and Digius Varus Minimi as seen from the top is shown. The first toe 4 (Hallux Valgus) is rotated about the first metatarasophalangeal joint 10 to abnormally approach the second, and the fifth toe 8 (Digitus Varus Minimi) is rotated about the fifth metatarsophalangeal joint 11 to abnormally approach the fourth.

Figure 8:
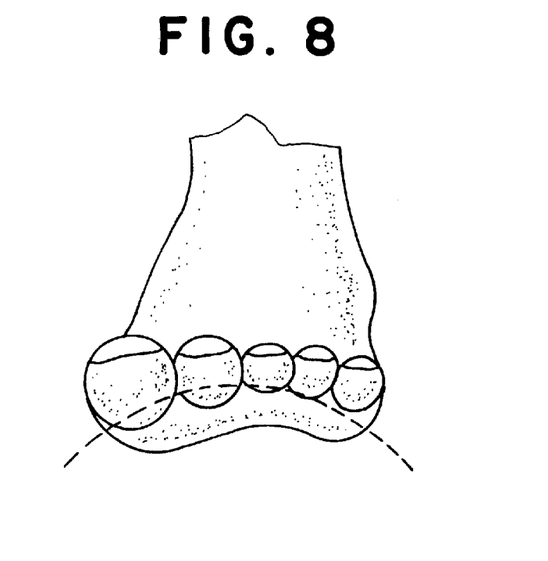
FIG. 8 is a front view of a foot with normal lateral arch form.
Figure 10:
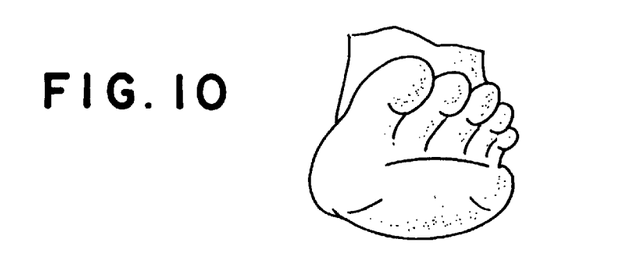
FIG. 10 is an external oblique view of a foot with no balance.
Figure 11:
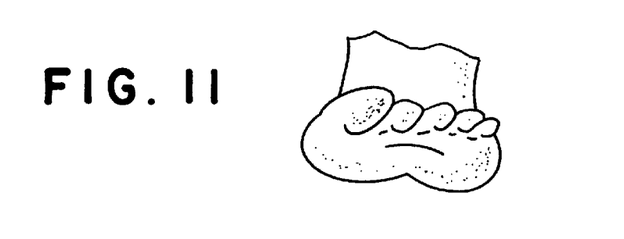
FIG. 11 is an external oblique view of a foot with normal lateral arch form.
Figure 12:
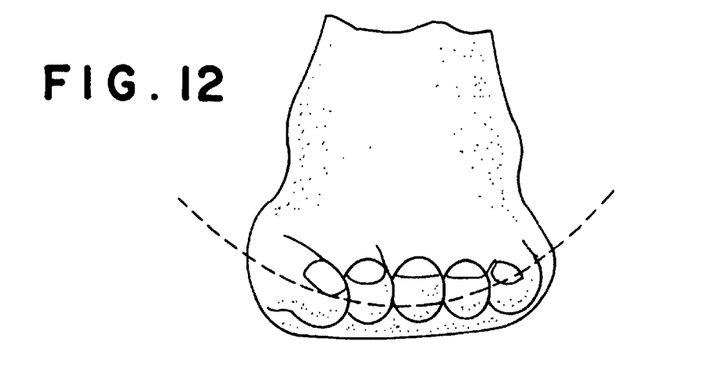
FIG. 12 is a front view of a foot with no plantar arch.

As also understood from FIG. 9, the distance between the first metatarsophalangeal joint 10 and the fifth 11 is abnormally lengthened. The deformed metatarsophalangeal joints produce the lateral metatarsal ligament, which is completely stretched out to cause the vertical and lateral arches of the sole to be deformed or disappeared to lose the function to maintain the movements in the human weight while using toes, as well as the function to absorb the shock and buckling waves, as shown in FIG. 10. (In FIG. 8 and FIG. 11, a foot, which is normally formed with the lateral arch is shown). The weight, which is applied to the deformed foot with Hallux Valgus is exerted on only the deformed or disappeared plantar arch. (In FIG. 12, a foot with a flat sole as seen from the front is shown). For this reason, the body is adversely affected by the foot which is susceptible to the shock and buckling waves (vertical and lateral waves as caused by earthquakes) that are generated strongly during walking of the walker.

In most of cases, Hallux Valgus and Digitus Varus Minimi deformities are caused by narrow fashion shoes such as high heeled shoes, sandals and the others that are worn by many women. These days, not so many young men than women walk with the narrow fashionable shoes. They also suffer from their deformed foot.

Figure 13:
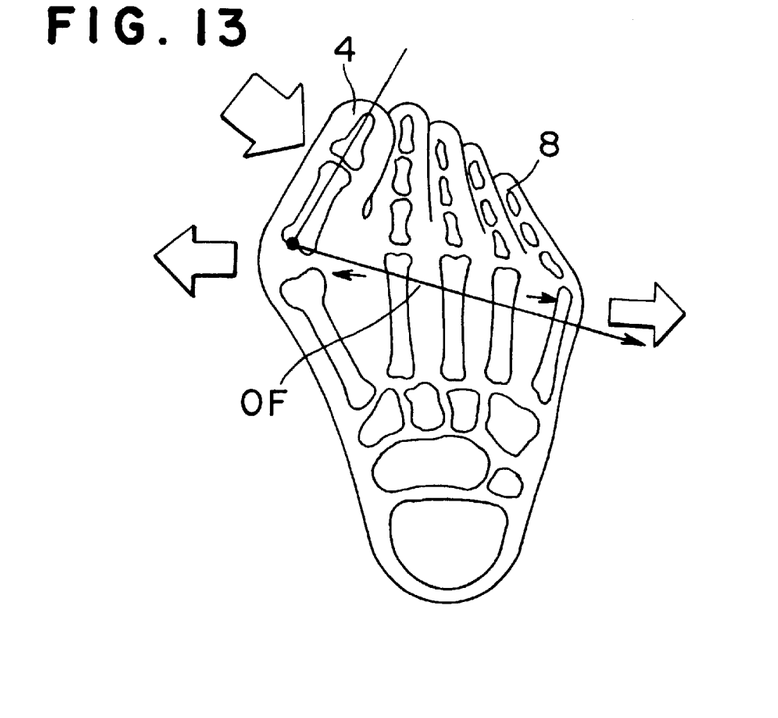
FIG. 13 is a plan view which illustrates Hallux Valgus and Digitus Varus Minimi associated deformities of a skeleton of a foot.

Referring to FIG. 13, a top view of a right foot with an abnormally deformed skeleton is shown. It is known that the rotations of the proximal phalanxes of phalanges about the metatarsophalangeal joints 10 act on the free inward and outward movements of the toes with respect to the median human body line.

Suppose, for example, that a wearer's foot is put in a narrow shoe. The side wall of the shoe forces against the first toe to hurt the wearer, and thereby the first toe is outwardly displaced with respect to the median human body line or approaches the second toe. As a result of the rotation of the first toe about the first metatarsophalangeal joint, leverage is produced, in which the first toe becomes the point where force is applied, while the proximal first toe end becomes its fulcrum, and thereby abnormal inward protrusion of the first metatarsophalangeal joint relative to that which is at the correct position results (Hallux Valgus).

The force, which is applied to the fulcrum is exerted next to the application point, which is at the fifth metatarsus to the outer ankle. The fifth metatarsus is outwardly rotated about the proximal joint by the outward force OF so that the fifth metatarsophalangeal joint 11 comes off the opposite side, and the fifth toe is inwardly rotated about the fifth metatarsophalangeal joint 11 to approach the fourth (Digitus Varus Minimi).

It can be said that the most serious problem with the Hallux Valgus is that the body is susceptible to the harmful buckling waves, which are strengthened by the outward force OF. When a foot with Hallux Valgus is brought into contact with and separation from the earth during walking, the body has a tendency to be outwardly laterally located to the earth with respect to the correct positions by the outward force, and the front foot has a tendency to be outwardly rotated about the ankle. Portions of the legs to the body of the person are also outwardly laterally forced with respect to the correct positions by the outward force, and thereby the body is distorted, or a pair of pelvis or legs are located at different heights from the earth relatively to each other. Thus, the buckling waves, which are generated in the foot with Hallux Valgus cause the right and left difference and are very injurious to the person.

The reproductions of the vertical and lateral arches minimizing generations of those shock and buckling waves are accomplished by curing processes which reduce the inter-metatarsal distance such that the first toe and the fifth are separated from the second and the fourth, respectively.

Figure 5:
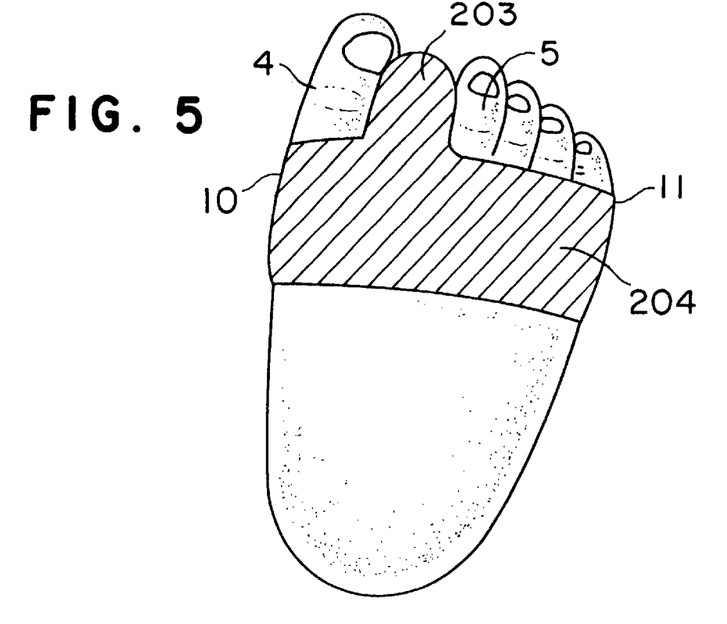
FIG. 5 is a top plan view of the first conventional corrective supporter which is fitted on a foot.

Referring to FIG. 5, a top plan view of a known corrective supporter pertinent to the instant application is shown (Japanese publication No. 7-13699 of examined utility Model application, Registration No. 2097115, and Japanese publication No. 7-27926 of examined utility model application, Registration No. 2111081). The first to fifth metatarsi are tightly bandaged by a pushing band 204 forming a ring, which grips the foot. Thus, the intermetatarsal distance is reduced. In addition, the first toe 4 is separated from the second toe 5 by a resilient reinforcement 203 extending from the front edge of the pushing band 204 between the first toe and the second.

Figure 6:
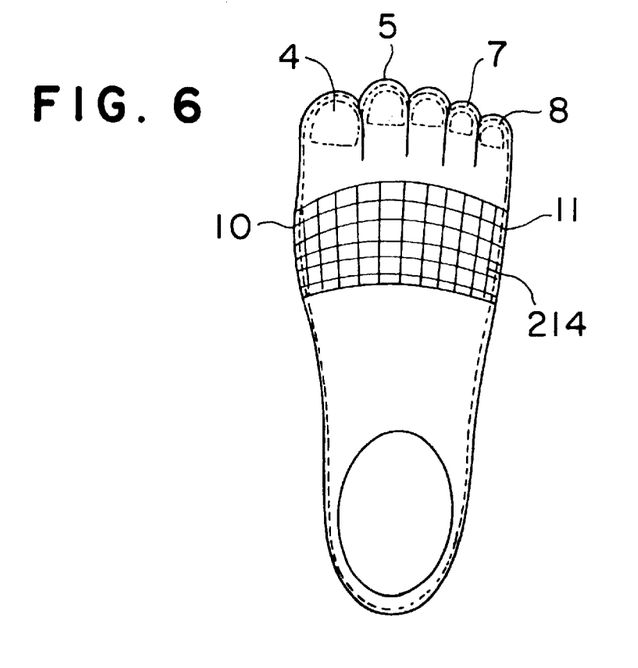
FIG. 6 is a top plan view of the second conventional corrective supporter as applied to a sock.

Referring to FIG. 6, a top plan view of a second known corrective supporter which is used to a sock, is shown (Japanese Utility Model Registration No. 2534781). The first to fifth metatarsi 10 to 11 are tightly bandaged by a pushing band 214 which is of high strength in contractions relatively to the other portions of the sock.

Figure 7:
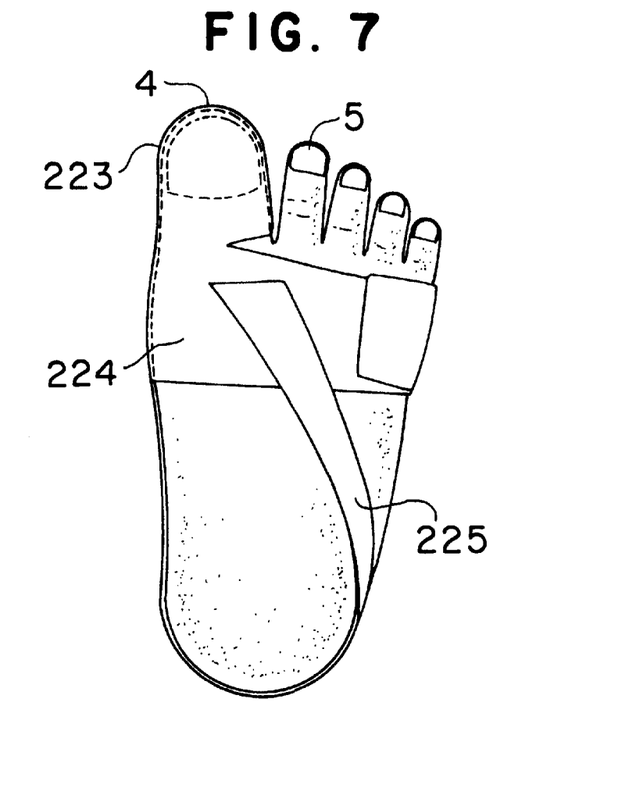
FIG. 7 is a top plan view of the third conventional corrective supporter into which a foot is fitted.

Referring to FIG. 7, a top plan view of a third known corrective supporter is shown (Japanese publication No. 7-12094 of examined patent application, Patent No. 158761). The first to fifth metatarsi are tightly bandaged by a pushing band 224. The pushing band 224 is wound about the foot side to side and fastened by a pair of velvet faster, one of which is formed on the whole band surface and the other of which is formed on the distal band surface end. The first toe 4 is fit into a tubular holder 223 extending from the front edge of the band 224. The tubular holder 223 is pulled by a pulling band 225 such that the first toe 4 moves away from the second 5. The pulling force of the tubular holder 223 is adjustably applied by removably adhering the pulling band 225 to the velvet faster surface of the pushing band.

A problem with the above corrective supporters is that the respective pushing bands often slip on the foot surface while laterally rotating by the outward force OF (FIG. 13) each in response to contacts and separations of the plantar sole with and from the earth during walking of the person.

Figure 14:
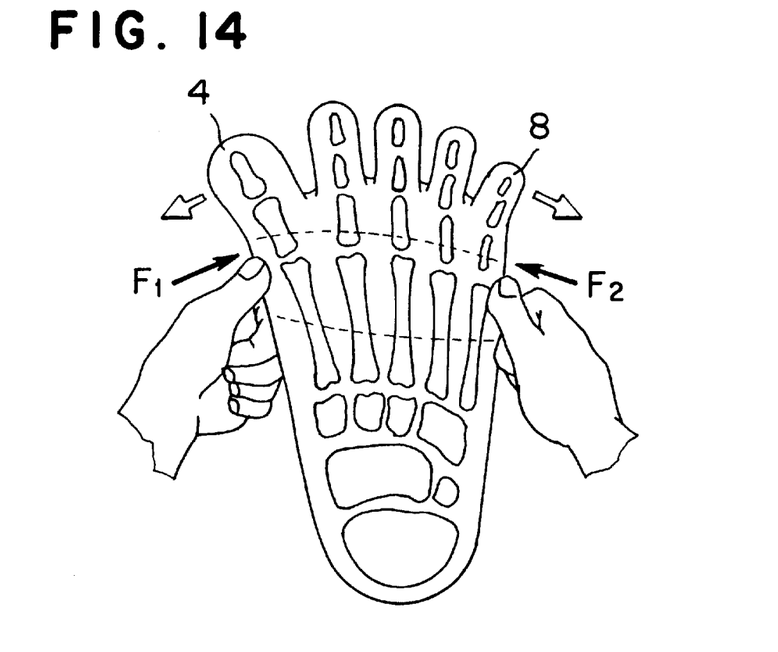
FIG. 14 is a plan view which illustrate a skeleton of a normal and corrected foot.

The above invention as shown in FIG. 6 contemplates pushing against both the side first metatarsophalangeal joint 10 and the fifth 11 by the respective pushing force F1 and F2, which cause the first toe 4 and the fifth 8 to be separated from the second and the fourth, respectively as shown in FIG. 14. The above inventions as shown in FIG. 5 and 7 each is intended to reinforce only the separation of the first toe from the second by the reinforcement which is between the first and the second. However, their corrective forces are not sufficiently exerted in minimizing the generation of the respective shock and buckling waves which travel to the body from the foot.

SUMMARY OF THE INVENTION

The improved corrective supporter of the present invention has a pushing band for laterally pushing the intermetatarsophalangeal joints to substantial proximal metatarsal end area for protecting the outer and inner vertical, and lateral arches, and a pair of resilient reinforcements, the first resilient reinforcement extending beyond the front edge of the pushing band at the suitable position and formed in a shape such that the separation of the first toe from the second is performed for reinforcing the correction of Hallux Valgus, and the second reinforcement extending beyond the front edge of the pushing band at the suitable position, which is between the fifth toe and the fourth and formed in a shape such that the separation of the fifth toe from the fourth toe is performed for reinforcing the correction of Digitus Varus Minimi deformity.

Two embodiments of the corrective supporter are disclosed herein. The corrective supporter in accordance with the first embodiment is of a construction in which the first and second corrective members are of resilient projections which are fitted between the first toe and the second, and between the fifth and the fourth of the foot, respectively. The side of the first resilient projection laterally pushes against the first toe to cause the first toe to be inwardly separate from the second so as to correct Hallux Valgus deformity, while the side of the second resilient projection pushes against the fifth toe to cause the fifth toe be outwardly separated from the fourth so as to correct Digitus Varus Minimi deformity.

Thus, the side of the second resilient projection pushes against the fifth toe which might approach the fourth in response to the pushing band that will slip on the foot surface by the outward force during walking of the person. The lateral ligament, which is stretched out is widthwise reduced more effectively by the separation of the fifth toe from the fourth by the second resilient projection as well as the separation of the first toe from the second by the first resilient projection, and thereby the lateral arch is formed between the first toe and the fifth. The formation of the lateral arch protects against slips of the pushing band that might be caused by the outward force generated in response to deformation of the plantar arch.

The corrective supporter in accordance with the second embodiment is of a very simple construction, which comprises a resilient material and has a pushing band for pushing the first and the fifth metatarsophalangeal joint, and first and second tubular holders formed integrally with the pushing band as the first and second reinforcements so as to hold the first toe and the fifth therein, respectively.

The first and second tubular holders are of shapes which are inclined laterally inwardly, or outwardly at the suitable angle with respect to the second toe, and the fourth from the corresponding positions to the basic first and second toes, respectively. Upon putting the first toe and the fifth into the first tubular holder and the second, the first toe and the fifth move away from the second and the fourth by the outward resilient pull force applied by the fist tubular holder and the second, respectively, and thereby both corrections of Hallux Valgus and Digitus Varus Minimi deformity are made. It will be understand from the foregoing that the corrective supporter enables to reduce even increase in the width of the intermetatarsal ligament, that is caused when the intermetatarsal ligament is completely stretched by Digits Varus Minimi. This results in more effectively maintaining the shape of the plantar arch obtained by the push of the pushing band against both the first metatarsophalangeal joint and the fifth.

DETAILED DESCRIPTION OP THE PREFERRED EMBODIMENT

The primary viewpoint of the instant invention is to allow more effective corrections of Hallux Valgus and Digitus Varus deformities in combination of pushing forces F1, F2 of the pushing band against the prominent first and fifth metatarsophalangeal joints with the individual separations of the toes, as shown in FIG. 14.

The description of the instant invention will be in relationship with two embodiments of the corrective supporter, which allows corrections of Hallux Valgus and Digitus Varus Minimi deformities. References of the first and second embodiments are made to FIGS. 1 to 3 and FIG. 4, respectively.

Embodiment 1

Figure 1:
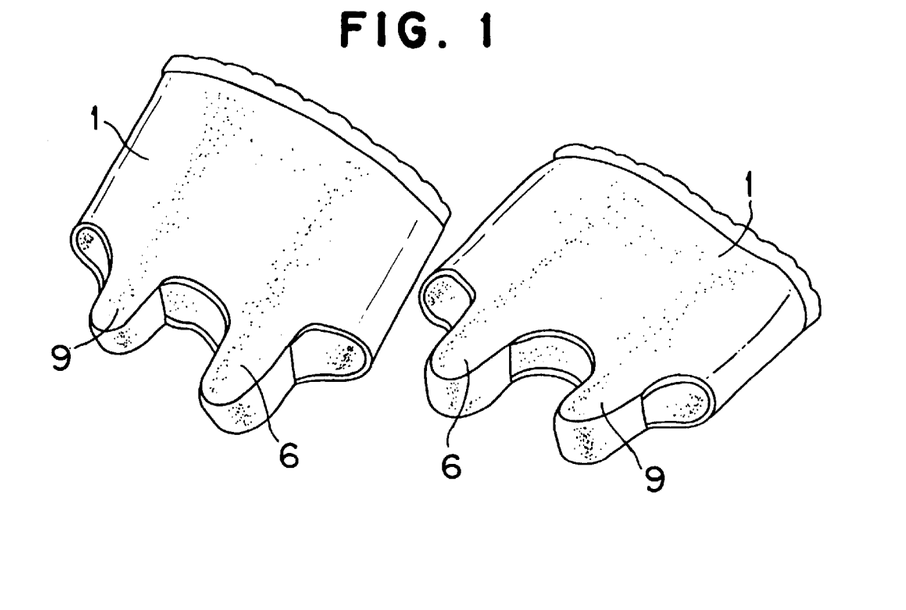
FIG. 1 is an external oblique view which illustrates right and left corrective supporters in accordance with the first embodiment of the instant invention for correcting Hallux Valgus and Digitus Varus Minimi deformities.

Referring to FIG. 1, there are shown right and left corrective supporters, each of which has a pushing band 1 which is tightly fastened on a foot surface, a first elastic projection 6 extending beyond the front edge of the pushing band 1 at a suitable position which is between the first toe and the second, and a second elastic projection 9 extending beyond the front edge of the pushing band 1 at a suitable position which is between the fifth toe and the fourth.

Figure 2:
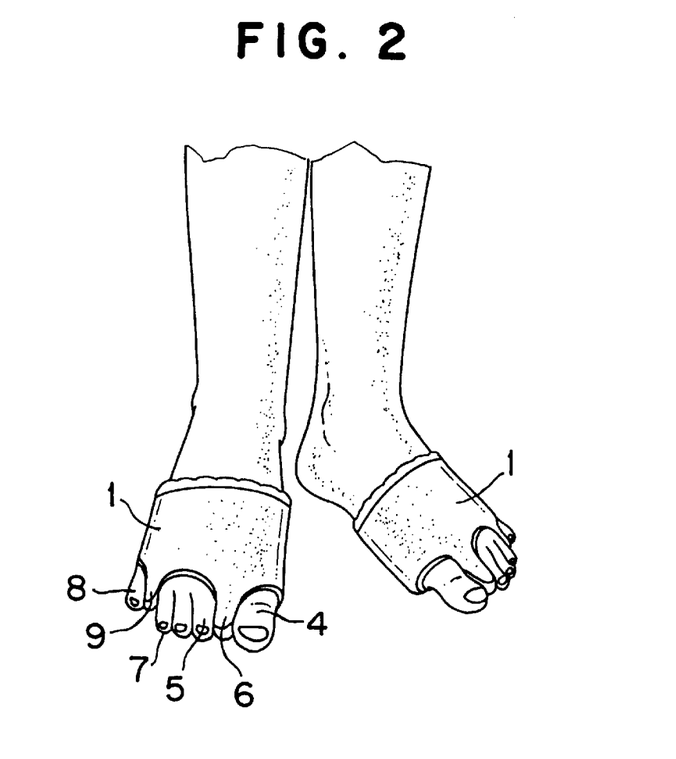
FIG. 2 is an external oblique view which illustrates the supporter of FIG. 1, into which a foot is put.

FIG. 2 illustrates the corrective supporters worn on the feet of the wearer. Each of the corrective supporters has three openings at the front, as seen from FIG. 1. The three opening comprises a first opening thorough which the first toe 4 projects, a second opening through which the second toe to the fourth 5 to 7 project, and a third opening through which the fifth toe 8 projects. The first resilient projection 6 fits between the first toe 4 and the second 5, while the second resilient projection 9 fits between the fifth toe 8 and the fourth 7. The pushing band 1 is fitted to cover the area which is at the toe bases to substantial the proximal metatarsal ends. A band with a pair of Velcro (Registered Trademark) fasteners may be applied to the pushing band 1, similar to the conventional corrective supporters.

Figure 3:
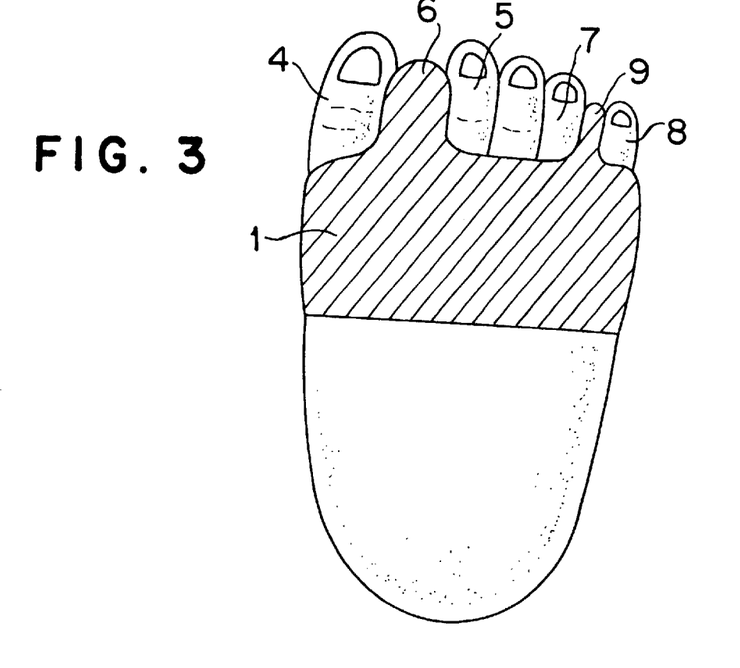
FIG. 3 is a plan view of the supporter of FIG. 1.

Thus, as shown in FIG. 3, when the corrective supporters fit the feet of the wearer, the side of the first resilient projection laterally pushes inwardly with respect to the second toe against the first toe to allow movement of the first toe away from the second, while the side of the second elastic projection laterally outwardly pushes with respect to the fourth toe against the fifth toe to allow movement of the fifth away from the fourth.

Furthermore, the projection of the toes from the respective openings permits the wearer to feel comfort during walking, because of touching of the second 5 to fourth 7 toes on the bottom. Accordingly, the wearer can walk well.

Embodiment 2

Figure 4:
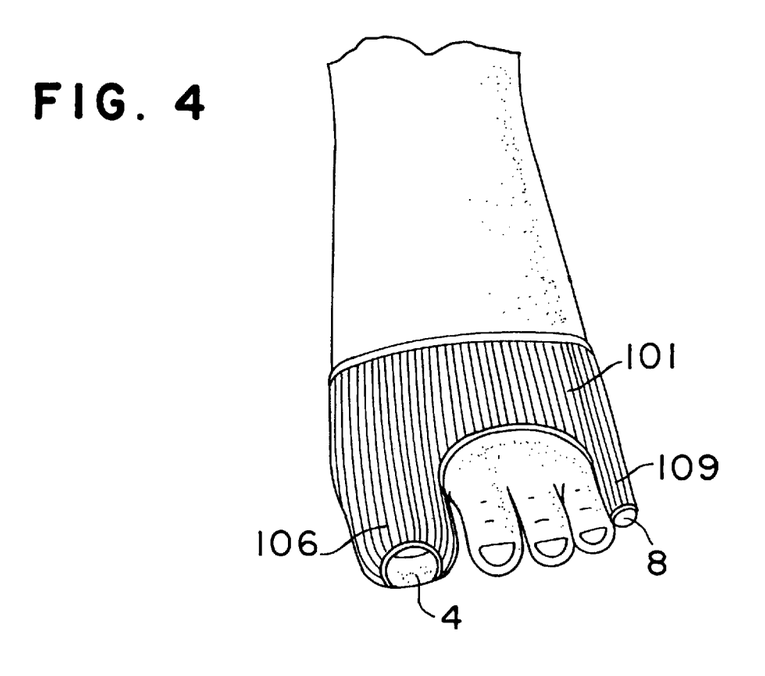
FIG. 4 is an external oblique view which illustrates one corrective supporter in accordance with the second embodiment of the instant invention, with which a foot is fitted.

Referring to FIG. 4, there is shown a corrective supporter in accordance with the second embodiment. The corrective supporter comprises a resilient material and has a pushing band 101 and two tubular holders, the first tubular holder 106 being shaped to contain the first toe 4, and the second tubular holder 109 being shaped to contain the fifth toe 8.

As shown in the figure, when each corrective supporter is fitted on a wearer's foot the pushing band holds the area at the toe bases to the substantial proximal metatarsi such that the resilient push force pushes against the prominent first and fifth metatarsophalangeal joints 10 and 11 respectively.

The first tubular holder 106 and the second 109 are formed integrally with the pushing band 101 and extend forwardly beyond the front edge of the pushing band 101 at the corresponding positions to the first and fifth toes 4 and 8, respectively.

The first and second tubular holders 106 and 109 are inwardly and outwardly inclined from the corresponding position to the basic first and fifth toes 4 and 8 with respect to the second and fourth toes 5 and 7, respectively. The inclination produces outward resilient pull by the first and second tubular holders 106 and 109 such that the first and fifth toes 4 and 8 move away from the second and fourth toes 5 and 7, respectively.

Furthermore, each of the first tubular holder 106 and the second 109 is formed with an opening at the front. The first toe 4 and the fifth 8 are fitted into the first and second tubular holders 106 and 109 such that the distal toe ends slightly project from the opening, respectively. The front edge of the pushing band 101 is curved between the first and second tubular holders 106 and 109 to provide a rearward curved surface to allow free movement of the second to fourth toes 5 to 7.

Thus, the pushing band 101 pushes the prominent distal first metatarsophalangeal joint 10 and the prominent distal fifth metatarsophalangeal joint 11, and the first tubular holder 106 and the second 109 allow the inward separation of the first toe 4 from the second 5 and the outward separation of the fifth 8 from the fourth 7, respectively. In addition, the curved surface of the pushing band 101 permits the second to fourth toes 5 to 7 to move freely. The combination of the opening which causes the protruding second to the fourth toes 5 to 7 to be brought into contact with the bottom of the shoe or sock along with the distal holder ends from which the distal first and fifth toe ends slightly outwardly projects therefrom, respectively permit the wearer to feel comfort. Accordingly, the wearer can walk well.

What is claimed is:

1. A corrective supporter for correcting Hallux Valgus and Digitus Varus Minimi of a foot comprising a tubular pushing band encircling the foot at an area which extends from the toe bases to substantially the proximal metatarsal ends for pushing against the outward prominent first and fifth intermetatarsophalangeal joints on the foot surface, said pushing band having a front edge portion juxtaposed to the toe bases, a first resilient reinforcement projection attached to or formed integrally with said front edge portion of said pushing band and extending forwardly beyond the front edge portion of said pushing band at a position between the first toe and the second toe, a second resilient reinforcement projection attached to or formed integrally with said front edge portion of said pushing band and extending forwardly beyond the front edge portion of said pushing band at a position between the fifth toe and the fourth toe, said first resilient reinforcement projection resiliently pushing said first toe away from the second toe to correct Hallux Valgus, said second resilient reinforcement projection resiliently pushing said fifth toe away from the fourth toe to correct Digitus Varus Minimi, said first and second reinforcement resilient projections cooperating to provide resilient engagement with the foot at plural locations between said first and second toes and between said fifth and fourth toes to thereby prevent slippage of the corrective supporter on the foot during walking.

2. A corrective supporter according to claim 1 wherein said front edge portion has a first opening juxtaposed to said first resilient reinforcement projection through which said first toe projects, said front edge portion having a second opening juxtaposed to said second resilient reinforcement projection through which said fifth toe projects, said front edge portion having a third opening disposed between said first and second resilient reinforcement projections through which said second, third and fourth toes project.

3. A corrective supporter according to claim 2 wherein said second to fourth toes in said third opening are urged into contact with one another by said first and second resilient reinforcement projections.

4. A corrective supporter according to claim 2 wherein said front edge portion has a lower part disposed underneath the foot, said second to third toes projecting forwardly from said lower part such that the bottom of the second to third toes are exposed for engagement with an underlying surface.

5. A corrective supporter according to claim 1 wherein said first reinforcement projection has a forward terminating end which is disposed closer to the forward terminating end of the first toe than to the base of the first toe and said second reinforcement projection has a forward terminating end which is disposed closer to the forward end of the fourth toe than to the base of the fourth toe.

6. A corrective supporter for correcting Hallux Valgus and Digitus Varus Minimi of a foot comprising a resilient tubular pushing band encircling the foot at an area which extends from the toe bases to substantially the proximal metatarsal ends for pushing against the outward prominent first and fifth intermetatarsophalangeal joints on the foot surface, said pushing band having a front edge portion juxtaposed to said toe bases, a resilient first tubular holder which is attached to or formed integrally with said front edge portion and extends beyond the front edge portion at a position corresponding to the position of the first toe, and a second resilient tubular holder which is attached to or formed integrally with said front edge portion and extends beyond the front edge portion at a position corresponding to the fifth toe, the first resilient tubular holder being constructed to bias the first toe away from the second toe to thereby correct Hallux Valgus, and the second resilient tubular holder being constructed to biase the fifth toe away from the fourth toe to thereby correct Digitus Varus Minimi.

7. A corrective supporter according to claim 6 wherein said first tubular holder is a generally cylindrical resilient tube which fits around the first toe and which has a cylindrical axis which is inclined in a direction to resiliently urge said first toe away from said second toe, said second tubular holder being a generally cylindrical resilient tube which fits around said fifth toe and which has a cylindrical axis which is inclined in a direction to resiliently urge said fifth toe away from said fourth toe.

8. A corrective supporter according to claim 7 wherein said cylindrical axis of said first resilient tube and said cylindrical axis of said second resilient tube are each inclined at an acute angle relative to a vertical plane extending from the rear to the front of an erect human body and containing the median human body line.

* * * * *